United States Patent
Tsukamoto

(10) Patent No.: US 9,975,964 B2
(45) Date of Patent: May 22, 2018

(54) ANTIBODY AGAINST ALOPECIA-INDUCING SUBSTANCE AS ANTIGEN, COMPOSITION AND PRODUCTION METHOD

(71) Applicant: OSTRICH PHARMA KK, Kyoto (JP)

(72) Inventor: Yasuhiro Tsukamoto, Osaka (JP)

(73) Assignee: OSTRICH PHARMA KK, Kyoto (JP)

( * ) Notice: Subject to any disclaimer, the term of this patent is extended or adjusted under 35 U.S.C. 154(b) by 0 days. days.

(21) Appl. No.: 15/100,841

(22) PCT Filed: Dec. 2, 2014

(86) PCT No.: PCT/JP2014/006028
§ 371 (c)(1),
(2) Date: Jun. 1, 2016

(87) PCT Pub. No.: WO2015/083375
PCT Pub. Date: Jun. 11, 2015

(65) Prior Publication Data
US 2016/0297894 A1    Oct. 13, 2016

(30) Foreign Application Priority Data
Dec. 2, 2013    (JP) .................. 2013-249672

(51) Int. Cl.
| | | |
|---|---|---|
| C07K 16/40 | (2006.01) | |
| A61K 39/395 | (2006.01) | |
| C07K 16/02 | (2006.01) | |
| C07K 16/26 | (2006.01) | |
| A61K 8/98 | (2006.01) | |
| A61Q 7/00 | (2006.01) | |
| A61K 8/64 | (2006.01) | |
| C07K 16/44 | (2006.01) | |
| A61Q 5/02 | (2006.01) | |

(52) U.S. Cl.
CPC .............. *C07K 16/40* (2013.01); *A61K 8/64* (2013.01); *A61K 8/98* (2013.01); *A61K 39/3955* (2013.01); *A61K 39/39583* (2013.01); *A61Q 5/02* (2013.01); *A61Q 7/00* (2013.01); *C07K 16/02* (2013.01); *C07K 16/26* (2013.01); *C07K 16/44* (2013.01); *C07K 2317/11* (2013.01); *C07K 2317/23* (2013.01); *C07K 2317/76* (2013.01)

(58) Field of Classification Search
CPC ........ C07K 16/40; C07K 16/02; C07K 16/26; C07K 2317/76; C07K 2317/11; C07K 2317/23; A61K 39/3955; A61K 8/98; A61Q 7/00
See application file for complete search history.

(56) References Cited

U.S. PATENT DOCUMENTS

2009/0306347 A1    12/2009    Tsukamoto
2010/0203055 A1    8/2010    Imamura et al.

FOREIGN PATENT DOCUMENTS

| WO | WO 2007/026689 A1 | 3/2007 |
| WO | WO 2008/020490 A1 | 2/2008 |
| WO | WO 2008/102783 A1 | 8/2008 |
| WO | WO 2010/047103 A1 | 4/2010 |
| WO | WO 2012/057336 A1 | 5/2012 |

OTHER PUBLICATIONS

International Search Report for corresponding International Application No. PCT/JP2014/006028 dated Feb. 24, 2015.

*Primary Examiner* — Ruixiang Li
(74) *Attorney, Agent, or Firm* — Renner, Otto, Boisselle & Sklar, LLP

(57) ABSTRACT

Causes of hair loss have not been completely clarified and still remain unknown in many points. However, it appears that hair loss is partly caused by a mechanism wherein androgenic hormones in the scalp become active via the activation of DHT hormone by 5α-reductase and thus the activity of cells in hair roots is lost.

In the present invention, an antibody, said antibody being obtained by inoculating a female bird with 5α-reductase or DHT as an antigen, is administered to the scalp so that the activity of DHT is suppressed and the activity of cells in hair roots is elevated. This antibody can be used in the form of a composition together with other component(s), for example, as a hair tonic together with another hair growth promoter.

4 Claims, 2 Drawing Sheets

[Fig. 1]
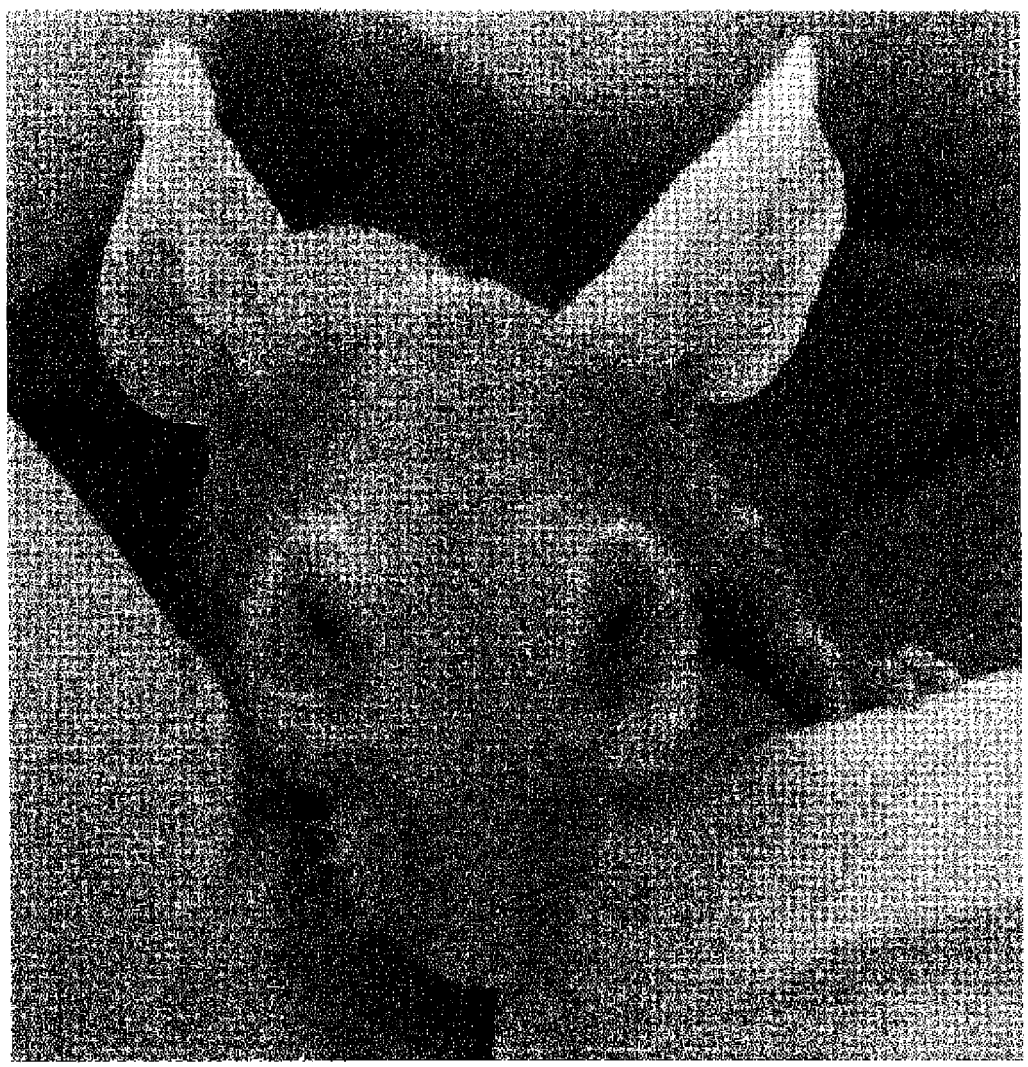

[Fig 2]
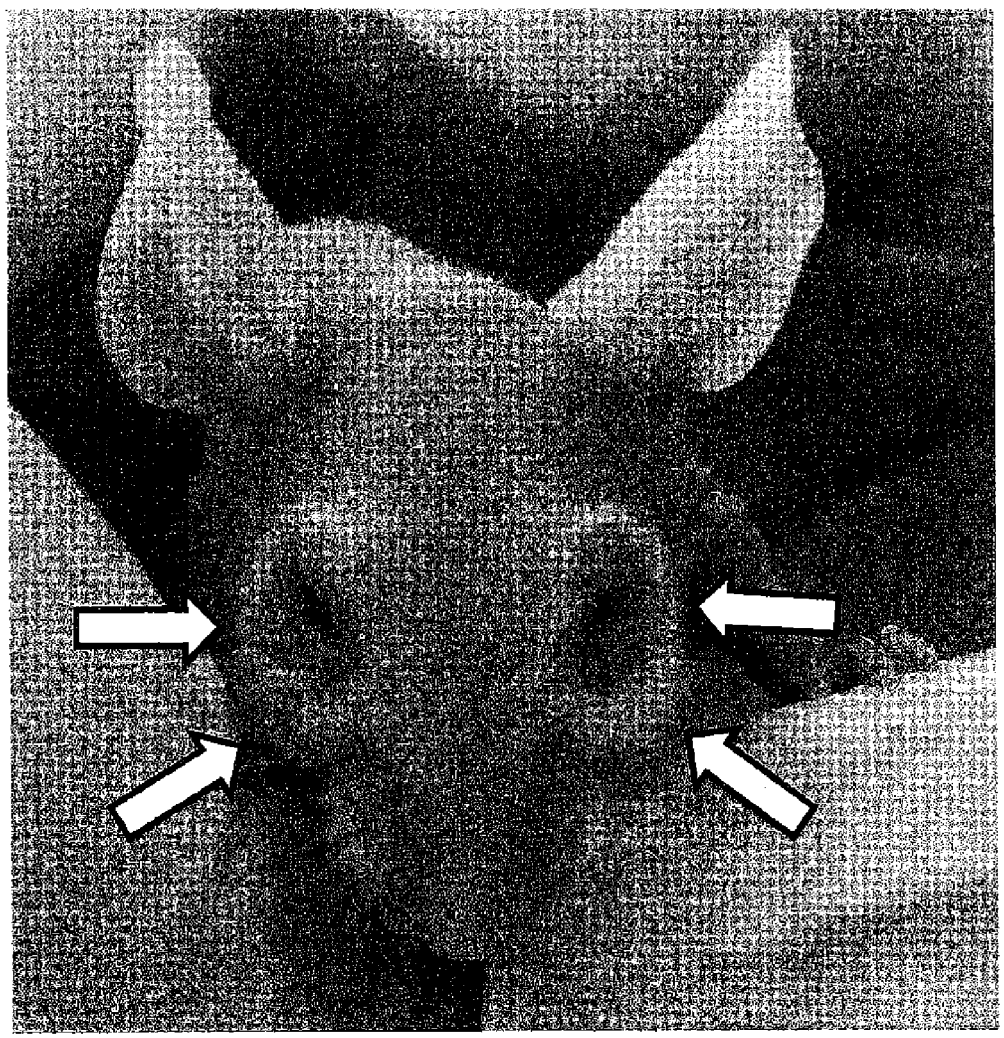

ANTIBODY AGAINST ALOPECIA-INDUCING SUBSTANCE AS ANTIGEN, COMPOSITION AND PRODUCTION METHOD

TECHNICAL FIELD

The present invention relates to an antibody obtained with a hair loss-inducing substance, which is considered as a cause for hair falling out, as an antigen and a composition having the antibody such as a hair growth agent or shampoo.

BACKGROUND ART

Many aspects of the alopecia-causing mechanism are not understood. In addition, a ground-breaking therapeutic method has not been discovered up to this point. The multi-factor nature of the causes due to differences in the living environment and individual differences is considered to be an obstructing factor for elucidating the causes. One conceivable cause of alopecia is the enzyme 5α-reductase converting an androgenic hormone, testosterone, into dihydrotestosterone (DHT) and the DHT acting on hair roots to lower hair producing activity.

Patent Literature 1 proposes artocarpin derivatives as an effective testosterone-5α-reductase activity inhibitor.

Further, Patent Literature 2 introduces known and novel compounds contained in Angelica atropurpurea as promoting hair growth by inhibiting NFAT (Nuclear factor of activated T cell) signals.

Several substances have also been proposed in Patent Literature 3 and the like from the viewpoint of hair growth promotion. Patent Literature 3 considers 3'-phosphoadenosine-5'-phosphosulfate as having an effect.

CITATION LIST

Patent Literature

[PTL 1] International Publication No. WO 2008/020490
[PTL 2] International Publication No. WO 2010/047103
[PTL 3] International Publication No. WO 2012/057336

SUMMARY OF INVENTION

Technical Problem

Currently, it appears that the causes of alopecia cannot be specified to one cause. However, a large amount of DHT is observed on the portion of skin where hair loss has occurred. Thus, it is conceivable that inhibition of DHT activity is very effective from the viewpoint of nullify one of the causes. One of the efficacies of conventional methods, however, was suppression of production or activity of these hormones. Thus, the methods do not directly suppress the activity of these hormones or enzymes. That is, there was a risk of side effects.

Solution to Problem

In view of the above-described problem, the present invention attempts to inhibit the activity of the enzyme (5α-reductase) or hormone (DHT), which is considered to be the cause of alopecia, by using an antibody to the enzyme or hormone.

More specifically, the composition of the present invention comprises an antibody obtained from an egg laid by female aves, which is inoculated with a hair loss-inducing substance as an antigen. The composition may also be a hair growth agent or a hair washing agent such as shampoo. Furthermore, the antibody itself can also be directly used.

Advantageous Effects of Invention

If antibodies are utilized, hair loss-inducing substances such as 5α-reductase or DHT can be blocked without aside effect. Such antibodies may be utilized as a composition such as a haircare agent (shampoo, hair treatment agent, pharmaceutical products such as a hair growth agent) and are considered to have an effect on hair loss prevention.

BRIEF DESCRIPTION OF DRAWINGS

FIG. 1 is a picture of the face of a nude mouse which had a solution of anti-5α-reductase antibodies applied around the eyes and found to have hair production.

FIG. 2 is a picture, in which arrows were added to the portions with hair production found in FIG. 1.

DESCRIPTION OF EMBODIMENTS

The antibody of the present invention and the composition and the manufacturing method thereof are explained hereinafter. The following explanation shows one embodiment of the present invention. The following embodiments and Examples may be modified within the intended scope of the present invention.

The present invention attempts to grow hair by using an antibody that selectively adheres to an enzyme (5α-reductase) or hormone (DHT) (hereinafter, referred to as "hair loss-inducing substance"), which is considered to be the cause of alopecia, to suppress activity of such an enzyme or hormone, such that hair production at hair roots is not inhibited.

Thus, the antibody may be concurrently used with minoxidil or adenosine-related compound, the above-described 3'-phosphoadenosine-5'-phosphosulfate, or the like that activates hair root function. Since these combinations lower the activity of a hair loss-inducing substance that inhibits the activity of hair roots to activate hair root function, a higher level of hair growth action can be expected.

Further, routinely blocking hair loss-inducing substances can facilitate prevention, or suppression of progression, of alopecia. Thus, the antibody can be included in hair washing agents. As used herein, a hair washing agent includes not only soap, shampoo, conditioners, and hair treatment agents, but also hair styling agents such as pomade.

As discussed above, the composition of the present invention is not particularly limited, as long as it contains an antibody obtained from ayes explained below. The composition can be any haircare product such as a hair growth agent, hair growth promoting agent, hair washing agent, or hair styling agent.

The antibody of the present invention can be obtained from an egg laid by a female bird by immunizing the female bird with a hair loss-inducing substance such as an enzyme or hormone considered to be a cause of alopecia as an antigen. Ayes are used because ayes have low homology with humans and are readily recognized as a foreign substance, and antibodies are readily produced.

A known method can be utilized for the step of immunizing female ayes. Various adjuvants can be utilized with an antigen upon immunization. Further, immunization may include priming followed by booster.

Aves that can be utilized are not particularly limited. For example, ostriches are useful because each egg is large, enabling a large amount of antibodies of the same lot to be purified. Hereinafter, antibodies indicate 5α-reductase or DHT. However, the concept of lowering the activity of hair loss-inducing substances directly with antibodies is in itself novel. Thus, when a hair loss-inducing substance that is not exemplified herein is newly discovered, antibodies may be produced with such a substance as an antigen.

EXAMPLES

Example 1

The following examines the reactivity of an antibody, which is obtained by immunizing aves with a hair loss-inducing substance as an antigen, to the hair loss-inducing substance.

<Reactivity of Egg Yolk Antibodies Made by using ostriches, Chickens, and Quails to Hair Loss-Inducing Substance>

Antibodies to a hair loss-inducing substance was made as follows. Mature female birds (ostriches, chickens, and quails) were used. Each of 50 μg of 5α-reductase and 50 μg of dihydrotestosterone (DHT) was mixed with 0.2 mL of Freund's Complete Adjuvant to prime the ostriches, chickens and quails. Five ostriches, five chickens, and five quails were individually inoculated with each antigen. The ostriches, chickens, and quails were inoculated with the same amount of antigens.

After priming, each bird was boosted with a mixture solution of 50 μg of each antigen and Freund's Incomplete Adjuvant in week 2 and week 4. Egg yolk antibodies (IgY) were purified from the egg yolk of eggs from each bird obtained in week 8 after priming. The reactivity of the obtained egg yolk antibodies was tested by ELISA (Enzyme-Linked Immuno Sorbent Assay).

Antibodies were purified by the following procedure. First, to the egg yolk of the obtained eggs, 5 times the amount of TBS (20 mM of Tris-HCl, 0.15 M of NaCl, 0.5% NaN$_3$) and the same amount of 10% dextran sulfate/TBS were added, and the mixture was stirred for 20 minutes.

1M of CaCl$_2$/TBS was then added in the same amount as the egg yolk, and the mixture was stirred and left standing for 12 hours. The mixture was then centrifuged for 20 minutes at 15000 rpm, and the supernatant was collected. In addition, ammonium sulfate was added such that the final concentration would be 40%, and the mixture was left standing for 12 hours at 4° C.

After the mixture was left standing for 12 hours, the mixture was centrifuged for 20 minutes at 15000 rpm, and the precipitates were collected. Finally, the precipitates in the same amount as the egg yolk were resuspended into TBS, and dialysis was performed with TBS. Antibodies (IgY) with a purity of 90% were able to be collected from each egg by the above method.

Reactivity of antibodies to a hair loss-inducing substance by ELISA was examined as follows. Solid phases of 10 μg of 5α-reductase and 10 μg of DHT were formed separately at each well of a 96-well ELISA plate (4 hours at room temperature). A serially diluted solution (undiluted solution is 2 mg/mL) of ostrich antibodies (mixture of antibodies from the egg yolk obtained from each 5 ostrich), chicken antibodies (mixture of antibodies from the egg yolk obtained from each 5 chicken), and quail antibodies (mixture of antibodies from the egg yolk obtained from each 5 quail) was then dripped into each well and reacted for 1 hour at room temperature.

After washing, HRP labeled-secondary antibodies to each antibody were reacted for 1 hour at room temperature. After thoroughly washing, a luminescent peroxidase assay kit (S-Bio SUMILON) was used to measure absorbance (450 nm) with a plate reader. The maximum dilution factor indicating 2 times the absorbance value or greater of egg yolk antibodies of each avian species prior to immunization are shown as the ELISA value. The results are shown in Table 1.

TABLE 1

| | ELISA value of egg yolk antibodies made from each aves | | |
|---|---|---|---|
| Antigen | Ostrich | Chicken | Quail |
| 5α-reductase | 404,800 | 102,400 | 102,400 |
| DHT | 404,800 | 51,200 | 102,400 |

It was found that egg yolk antibodies with a high level of sensitivity to each antigen was made by immunizing ostriches, chickens, and quails with 5α-reductase and DHT. Although each avian species was immunized with the same amount of antigens, large-sized ostriches in particular produced antibodies with the highest reactivity. That is, this indicates that highly sensitive antibodies can be produced with a small amount of antigens when an ostrich is used.

Example 2

50 μg of 5α-reductase was mixed with 0.2 mL of Freund's Complete Adjuvant for priming female ostriches. Five ostriches were individually inoculated with antigens. After priming, each female ostrich was boosted with a mixture solution of 50 μg of antigen and Freund's Incomplete Adjuvant in week 2 and week 4. Egg yolk antibodies (IgY) were purified from the egg yolk of ostrich eggs obtained in week 8 after priming. The obtained antibodies were anti-5α-reductase antibodies.

The obtained anti-5α-reductase antibodies were dissolved in phosphate buffered saline (PBS) to make an antibody solution with a concentration of 2 mg/mL. A total of 0.5 mL of the antibody solution was applied every other day around the eyes of 9-week old male nude mice. Similarly, only PBS was applied to 9-week old male nude mice as controls. A nude mouse is a mouse which genetically lacks a coat of hair on the entire body.

10 nude mice applied only with PBS and 10 nude mice applied with an antibody solution of anti-5α-reductase antibodies were prepared for an experiment. The ratio of individuals who were found to have apparent hair production/hair growth was calculated in week 2. The results are shown in Table 2.

TABLE 2

| | PBS only | Anti-5α-reductase antibodies |
|---|---|---|
| Ratio of individuals with hair growth (%) | 0 | 70 |

0 out of 10 mice were found to have hair production when only PBS was applied. Meanwhile, 7 out of 10 mice were found to have hair production when an antibody solution of anti-5α-reductase antibodies was applied. Apparent hair growth was found on a portion where an antibody solution was applied from about week 1 in the early cases.

FIG. 1 shows a picture of the face of a nude mouse in week 2 after starting application of an antibody solution. An area elevated like a pair of glasses can be seen around the eyes. The elevated area is the portion with hair production. FIG. 2 is the same picture indicating the portions with hair growth with arrows. In this manner, it was found that anti-5α-reductase antibodies have hair production/hair growth action by the mere application thereof.

INDUSTRIAL APPLICABILITY

The antibody of the present invention is considered to be capable of preventing alopecia because the antibody blocks hair loss-inducing substances such as 5α-reductase and DHT. Thus, the antibodies of the present invention can be widely utilized in compositions directed to alopecia.

The invention claimed is:

1. A method for hair production, hair growth, or hair production and hair growth in a subject, comprising providing an ostrich antibody against a hair loss-inducing substance as an antigen, and administering a therapeutically effective amount of the ostrich antibody to the subject, wherein the hair loss-inducing substance comprises 5α-reductase, dihydrotestosterone, or 5α-reductase and dihydrotestosterone.

2. The method of claim 1, wherein the hair loss-inducing substance comprises 5α-reductase.

3. The method of claim 1, wherein the hair loss-inducing substance comprises dihydrotestosterone.

4. The method of claim 1, wherein the hair loss-inducing substance comprises 5α-reductase and dihydrotestosterone.

* * * * *